US007470283B2

(12) United States Patent
Dutta

(10) Patent No.: US 7,470,283 B2
(45) Date of Patent: Dec. 30, 2008

(54) BIODEGRADABLE DRUG DELIVERY MATERIAL FOR STENT

(75) Inventor: Debashis Dutta, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 367 days.

(21) Appl. No.: 10/340,157

(22) Filed: Jan. 10, 2003

(65) Prior Publication Data

US 2003/0097173 A1    May 22, 2003

Related U.S. Application Data

(62) Division of application No. 09/548,533, filed on Apr. 13, 2000, now Pat. No. 6,527,801.

(51) Int. Cl.
*A61F 2/06* (2006.01)
(52) U.S. Cl. .................................... 623/1.46; 427/2.25
(58) Field of Classification Search ................ 623/1.13, 623/1.42, 1.43, 1.46, 1.18, 1.19, 1.38, 1.44, 623/1.12; 427/2.25; 424/426
See application file for complete search history.

(56) References Cited

U.S. PATENT DOCUMENTS

| | | | | |
|---|---|---|---|---|
| 3,839,743 A | 10/1974 | Schwarcz | ........................... | 3/1 |
| 3,900,632 A | 8/1975 | Robinson | .................... | 428/196 |
| 4,110,497 A | 8/1978 | Hoel | ......................... | 428/190 |
| 4,249,531 A * | 2/1981 | Heller et al. | ................. | 424/426 |
| 4,321,711 A | 3/1982 | Mano | ............................. | 3/1.4 |
| 4,346,028 A | 8/1982 | Griffith | ........................ | 524/417 |
| 4,633,873 A | 1/1987 | Dumican et al. | ............ | 128/334 |
| 4,656,083 A | 4/1987 | Hoffman et al. | ............ | 428/265 |
| 4,718,907 A | 1/1988 | Karwoski et al. | ............. | 623/12 |
| 4,722,335 A | 2/1988 | Vilasi | .................... | 128/207.14 |
| 4,723,549 A | 2/1988 | Wholey et al. | .............. | 128/344 |
| 4,732,152 A | 3/1988 | Wallstén et al. | ............. | 128/343 |
| 4,733,665 A | 3/1988 | Palmaz | ........................ | 128/343 |
| 4,739,762 A | 4/1988 | Palmaz | ........................ | 128/343 |
| 4,739,762 A | 4/1988 | Palmaz | ........................ | 606/108 |
| 4,740,207 A | 4/1988 | Kreamer | ......................... | 623/1 |
| 4,743,252 A | 5/1988 | Martin, Jr. et al. | .............. | 623/1 |
| 4,768,507 A | 9/1988 | Fischell et al. | .............. | 128/303 |
| 4,776,337 A | 10/1988 | Palmaz | ........................ | 128/343 |
| 4,816,339 A | 3/1989 | Tu et al. | ...................... | 428/421 |
| 4,850,999 A | 7/1989 | Planck | ............................ | 623/1 |
| 4,877,030 A | 10/1989 | Beck et al. | .................. | 128/343 |
| 4,878,906 A | 11/1989 | Lindemann et al. | ............. | 623/1 |
| 4,879,135 A | 11/1989 | Greco et al. | ..................... | 427/2 |
| 4,902,289 A | 2/1990 | Yannas | ............................ | 623/1 |
| 4,977,901 A | 12/1990 | Ofstead | ........................ | 128/772 |
| 4,994,298 A | 2/1991 | Yasuda | .......................... | 427/41 |
| 5,019,090 A | 5/1991 | Pinchuk | ....................... | 606/194 |
| 5,028,597 A | 7/1991 | Kodama et al. | ................ | 514/56 |
| 5,059,211 A | 10/1991 | Stack et al. | .................. | 606/198 |
| 5,062,829 A | 11/1991 | Pryor et al. | ..................... | 604/57 |
| 5,084,065 A | 1/1992 | Weldon et al. | .................. | 623/1 |
| 5,085,629 A | 2/1992 | Goldberg et al. | ................ | 604/8 |
| 5,100,429 A | 3/1992 | Sinofsky et al. | ............. | 606/195 |
| 5,108,755 A | 4/1992 | Daniels et al. | ............... | 424/426 |
| 5,112,457 A | 5/1992 | Marchant | ..................... | 204/165 |
| 5,123,917 A | 6/1992 | Lee | ................. | 623/1 |
| 5,156,623 A | 10/1992 | Hakamatsuka et al. | ......... | 623/11 |
| 5,163,951 A | 11/1992 | Pinchuk et al. | ................. | 623/1 |
| 5,163,952 A | 11/1992 | Froix | ............................. | 623/1 |
| 5,163,958 A | 11/1992 | Pinchuk | ....................... | 623/11 |
| 5,167,614 A | 12/1992 | Tessmann et al. | ............... | 604/8 |
| 5,192,311 A | 3/1993 | King et al. | ...................... | 623/1 |
| 5,197,977 A | 3/1993 | Hoffman, Jr. et al. | ........... | 623/1 |
| 5,234,456 A | 8/1993 | Silvestrini | .................... | 606/194 |
| 5,234,457 A | 8/1993 | Andersen | ..................... | 606/198 |
| 5,236,447 A | 8/1993 | Kubo et al. | ...................... | 623/1 |
| 5,279,594 A | 1/1994 | Jackson | ........................ | 604/265 |
| 5,282,860 A | 2/1994 | Matsuno et al. | ................ | 623/12 |
| 5,289,831 A | 3/1994 | Bosley | ......................... | 128/899 |
| 5,290,271 A | 3/1994 | Jernberg | ................... | 604/891.1 |
| 5,306,286 A | 4/1994 | Stack et al. | ................... | 606/198 |
| 5,306,294 A | 4/1994 | Winston et al. | ................. | 623/1 |

(Continued)

FOREIGN PATENT DOCUMENTS

DE    44 07 079    9/1994

(Continued)

OTHER PUBLICATIONS

Bull, *Parylene Coating for Medical Applications*, Medical Product Manufacturing News (Mar. 1993).

(Continued)

*Primary Examiner*—Julian W Woo
*Assistant Examiner*—Victor X Nguyen
(74) *Attorney, Agent, or Firm*—Squire Sanders & Dempsey LLP

(57) ABSTRACT

A stent is fabricated utilizing a polymer that is selected for its tendency to degrade from the surface inwardly rather than undergo bulk erosion so as to substantially reduce the risk of large particles becoming detached and being swept downstream. Such polymer is hydrophobic yet has water-labile linkages interconnecting the monomers. Ester or imide bonds are incorporated in the polymer to render the surface degrading materials suitable for use in stent applications. The stent may be coated with such polymer or may be wholly formed therefrom.

12 Claims, No Drawings

U.S. PATENT DOCUMENTS

| | | | |
|---|---|---|---|
| 5,328,471 A | 7/1994 | Slepian | 604/101 |
| 5,330,500 A | 7/1994 | Song | 606/198 |
| 5,342,348 A | 8/1994 | Kaplan | 604/891.1 |
| 5,342,395 A | 8/1994 | Jarrett et al. | 606/219 |
| 5,342,621 A | 8/1994 | Eury | 424/423 |
| 5,356,433 A | 10/1994 | Rowland et al. | 623/11 |
| 5,380,299 A * | 1/1995 | Fearnot et al. | 604/265 |
| 5,383,925 A | 1/1995 | Schmitt | 623/1 |
| 5,385,580 A | 1/1995 | Schmitt | 623/1 |
| 5,389,106 A | 2/1995 | Tower | 606/198 |
| 5,441,515 A | 8/1995 | Khosravi et al. | 606/194 |
| 5,443,458 A | 8/1995 | Eury | 604/891.1 |
| 5,455,040 A | 10/1995 | Marchant | 424/426 |
| 5,464,650 A | 11/1995 | Berg et al. | 427/2.3 |
| 5,502,158 A | 3/1996 | Sinclair et al. | 528/354 |
| 5,514,379 A | 5/1996 | Weissleder et al. | 424/426 |
| 5,527,337 A | 6/1996 | Stack et al. | 606/198 |
| 5,554,120 A | 9/1996 | Chen et al. | 604/96 |
| 5,578,073 A | 11/1996 | Haimovich et al. | 623/1 |
| 5,591,607 A | 1/1997 | Gryaznov et al. | 435/91.1 |
| 5,593,403 A | 1/1997 | Buscemi | 606/2 |
| 5,599,301 A | 2/1997 | Jacobs et al. | 604/65 |
| 5,599,922 A | 2/1997 | Gryaznov et al. | 536/25.3 |
| 5,605,696 A | 2/1997 | Eury et al. | 424/423 |
| 5,629,077 A | 5/1997 | Turnlund et al. | 442/38 |
| 5,631,135 A | 5/1997 | Gryaznov et al. | 435/6 |
| 5,637,113 A | 6/1997 | Tartaglia et al. | 623/1 |
| 5,649,977 A * | 7/1997 | Campbell | 623/1.15 |
| 5,667,767 A | 9/1997 | Greff et al. | 424/9.411 |
| 5,670,558 A | 9/1997 | Onishi et al. | 523/112 |
| 5,693,085 A | 12/1997 | Buirge et al. | 623/1 |
| 5,700,286 A | 12/1997 | Tartaglia et al. | 623/1 |
| 5,707,385 A | 1/1998 | Williams | 606/192 |
| 5,713,949 A * | 2/1998 | Jayaraman | 623/1.12 |
| 5,716,981 A | 2/1998 | Hunter et al. | 514/449 |
| 5,726,297 A | 3/1998 | Gryaznov et al. | 536/22.1 |
| 5,728,751 A | 3/1998 | Patnaik | 523/112 |
| 5,733,925 A | 3/1998 | Kunz et al. | 514/449 |
| 5,741,881 A | 4/1998 | Patnaik | 528/75 |
| 5,756,457 A | 5/1998 | Wang et al. | 514/12 |
| 5,756,476 A | 5/1998 | Epstein et al. | 514/44 |
| 5,766,710 A | 6/1998 | Turnlund et al. | 428/36.1 |
| 5,800,516 A | 9/1998 | Fine et al. | 623/1 |
| 5,811,447 A | 9/1998 | Kunz et al. | 514/411 |
| 5,824,049 A | 10/1998 | Ragheb et al. | 623/1 |
| 5,830,178 A | 11/1998 | Jones et al. | 604/49 |
| 5,830,461 A | 11/1998 | Billiar | 424/94.4 |
| 5,830,879 A | 11/1998 | Isner | 514/44 |
| 5,833,651 A | 11/1998 | Donovan et al. | 604/53 |
| 5,834,582 A | 11/1998 | Sinclair et al. | 528/354 |
| 5,837,313 A | 11/1998 | Ding et al. | 427/2.21 |
| 5,837,835 A | 11/1998 | Gryaznov et al. | 536/23.1 |
| 5,851,508 A | 12/1998 | Greff et al. | 424/9.411 |
| 5,854,207 A | 12/1998 | Lee et al. | 514/2 |
| 5,855,618 A | 1/1999 | Patnaik et al. | 623/11 |
| 5,858,746 A | 1/1999 | Hubbell et al. | 435/177 |
| 5,865,814 A | 2/1999 | Tuch | 604/265 |
| 5,873,904 A | 2/1999 | Ragheb et al. | 623/1 |
| 5,874,165 A | 2/1999 | Drumheller | 428/308.4 |
| 5,876,743 A | 3/1999 | Ibsen et al. | 424/426 |
| 5,877,263 A | 3/1999 | Patnaik et al. | 525/453 |
| 5,879,713 A | 3/1999 | Roth et al. | 424/489 |
| 5,891,192 A | 4/1999 | Murayama et al. | 623/1 |
| 5,897,955 A | 4/1999 | Drumheller | 428/422 |
| 5,914,182 A | 6/1999 | Drumheller | 428/308.4 |
| 5,916,870 A | 6/1999 | Lee et al. | 514/2 |
| 5,942,209 A | 8/1999 | Leavitt et al. | 424/1.25 |
| 5,948,428 A | 9/1999 | Lee et al. | 424/426 |
| 5,957,975 A | 9/1999 | Lafont et al. | 623/1 |
| 5,962,427 A * | 10/1999 | Goldstein et al. | 514/44 |
| 5,965,720 A | 10/1999 | Gryaznov et al. | 536/23.1 |
| 5,971,954 A | 10/1999 | Conway et al. | 604/96 |
| 5,980,564 A * | 11/1999 | Stinson | 623/23.7 |
| 5,980,928 A | 11/1999 | Terry | 424/427 |
| 5,980,972 A | 11/1999 | Ding | 427/2.24 |
| 5,981,568 A | 11/1999 | Kunz et al. | 514/411 |
| 5,997,468 A | 12/1999 | Wolff et al. | 600/36 |
| 6,015,541 A | 1/2000 | Greff et al. | 424/1.25 |
| 6,042,875 A | 3/2000 | Ding et al. | 427/2.24 |
| 6,048,964 A | 4/2000 | Lee et al. | 530/350 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,074,659 A | 6/2000 | Kunz et al. | 424/423 |
| 6,080,177 A | 6/2000 | Igaki et al. | 606/198 |
| 6,080,488 A | 6/2000 | Hostettler et al. | 428/423.3 |
| 6,093,463 A | 7/2000 | Thakrar | 428/36.9 |
| 6,096,070 A | 8/2000 | Ragheb et al. | 623/1 |
| 6,096,525 A | 8/2000 | Patnaik | 435/181 |
| 6,099,562 A | 8/2000 | Ding et al. | 623/1.46 |
| 6,103,230 A | 8/2000 | Billiar et al. | 424/94.4 |
| 6,107,416 A | 8/2000 | Patnaik et al. | 525/453 |
| 6,110,188 A | 8/2000 | Narciso, Jr. | 606/153 |
| 6,113,629 A | 9/2000 | Ken | 623/1.1 |
| 6,117,979 A | 9/2000 | Hendriks et al. | 530/356 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,127,173 A | 10/2000 | Eckstein et al. | 435/320.1 |
| 6,129,761 A | 10/2000 | Hubbell | 623/11 |
| 6,153,252 A | 11/2000 | Hossainy et al. | 427/2.3 |
| 4,776,337 A | 12/2000 | Palmaz | 606/108 |
| 6,159,951 A | 12/2000 | Karpeisky et al. | 514/45 |
| 6,165,212 A | 12/2000 | Dereume et al. | 623/1.13 |
| 6,166,130 A | 12/2000 | Rhee et al. | 525/54.1 |
| 6,169,170 B1 | 1/2001 | Gryaznov et al. | 536/23.1 |
| 6,171,609 B1 | 1/2001 | Kunz | 424/422 |
| 6,174,330 B1 | 1/2001 | Stinson | 623/1.34 |
| 6,177,523 B1 | 1/2001 | Reich et al. | 525/459 |
| 6,224,626 B1 | 5/2001 | Steinke | 623/1.16 |
| 6,228,845 B1 | 5/2001 | Donovan et al. | 514/44 |
| 6,245,103 B1 | 6/2001 | Stinson | 623/1.22 |
| 6,251,135 B1 | 6/2001 | Stinson et al. | 623/1.34 |
| 6,251,142 B1 | 6/2001 | Bernacca et al. | 623/23.57 |
| 4,733,665 C2 | 1/2002 | Palmaz | 606/108 |
| 6,626,939 B1 * | 9/2003 | Burnside et al. | 623/1.38 |
| 2004/0138260 A1 * | 7/2004 | Natchus et al. | 514/317 |
| 2006/0136051 A1 * | 6/2006 | Furst et al. | 623/1.42 |

FOREIGN PATENT DOCUMENTS

| | | |
|---|---|---|
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 970 711 | 1/2000 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 95/29647 | 11/1995 |

| | | |
|---|---|---|
| WO | WO 00/12147 | 3/2000 |
| WO | WO 00/64506 | 11/2000 |
| WO | WO 01/01890 | 1/2001 |

OTHER PUBLICATIONS

Casper et al., *Fiber-Reinforced Absorbable Composite for Orthopedic Surgery*, Polymeric Materials Science and Engineering, 53:497-501 (1985).

Devanathan et al., *Polymeric Conformal Coatings for Implantable Electronic Devices*, IEEE Transactions on Biomedical Engineering, vol. BME-27(11):671-675 (1980).

Hahn et al., *Biocompatibility of Glow-Discharged-Polymerized Films and Vacuum-Deposited Parylene*, J. Applied Polymer Sci, 38:55-64 (1984).

Hahn et al., *Glow Discharge Polymers as Coatings for Implanted Devices*, ISA, pp. 109-111 (1981).

Kelley et al., *Totally Resorbable High-Strength Composite Material*, Advances in Biomedical Polymers, 35:75-85 (1987).

Kubies et al., *Microdomain Structure in Polylactide-block-poly(ethylene oxide) Copolymer Films*, Biomaterials 21:529-536 (2000).

Muller et al., *Advances in Coronary Angioplasty: Endovascular Stents*, Coron Arter Dis, 1(4):438-448 (Jul./Aug. 1990).

Nichols et al., *Electrical Insulation of Implantable Devices by Composite Polymer Coatings*, ISA Transactions, 26(4):15-18 (1987).

Schatz, *A View Vascular Stents*, Circulation, 79(2):445-457 (Feb. 1989).

Schmidt et al., *Long-Term Implants of Parylene-C Coated Microelectrodes*, Med & Biol Eng & Comp, 26(1):96-101 (Jan. 1988).

\* cited by examiner

BIODEGRADABLE DRUG DELIVERY MATERIAL FOR STENT

This is a divisional application of U.S. Ser. No. 09/548,533, which was filed on Apr. 13, 2000 now U.S. Pat. No. 6,527,801.

BACKGROUND OF THE INVENTION

The present invention generally relates to expandable intraluminal vascular grafts, most often referred to as stents, and more particularly pertains to biodegradable stents which completely or partially degrade or are bioabsorbed over a period of time after deployment.

Stents are used to maintain the patency of vessels in the body. They are typically advanced through the vasculature to the deployment site while in a contracted state where they are then expanded to engage the vessel walls and thereby establish a flowpath therethrough. A stent can be moved along a guide wire previously positioned in the vessel and then expanded by the inflation of a balloon about which such stent is disposed. Subsequent deflation of the balloon and removal of it along with the guidewire leaves the stent in place and locked in its expanded state. It has been found that the continued exposure of a stent to blood can lead to undesirable thrombus formation, and the presence of a stent in a blood vessel can over time cause the blood vessel wall to weaken, which creates the potential for an arterial rupture or the formation of aneurisms. A stent can also become so overgrown by tissue after its implantation that its usefulness may be substantially diminished while its continued presence may cause a variety of problems or complications.

In certain situations it is therefore desirable for the stent to be biodegradable or bioabsorbable so as to curtail the adverse risks that would otherwise be associated with the stent's continued presence once its usefulness at the treatment site has ceased or has at least become substantially diminished. To such end, some stents have heretofore been wholly constructed of materials that are biodegradable or bioabsorbable. It is of course necessary to select a material that while biodegradable is nonetheless biocompatible and additionally, has the physical properties necessary to properly serve its function as a stent. Such physical properties include, among others, sufficient strength to support the loads a particular stent is to be subjected to in its function as a splint, the radial flexibility necessary for it to undergo expansion, longitudinal flexibility to allow it to be advanced through a contorted vasculature and conceivably to adapt to a non-linear deployment site.

Such characteristics have heretofore been achieved with the use of certain polymer materials such as polylactic acid, polylactic acid-glycolic acid copolymer, and polycaprolactone. However, all such previously known biodegradable/bioabsorbable stents exhibit bulk erosion and are as a consequence prone to break up into large particles as the matrix breaks down. Additionally, such materials have also been used as stent coatings to gradually release pharmacological agents that are infused throughout the coating. However, the bulk erosion to which such materials are inherently prone to can cause the coating to flake off or otherwise become detached. Should such large particles actually become dislodged before becoming completely degraded, they could be washed downstream and cause emboli.

A biodegradable stent is therefore needed that is initially capable of providing the necessary structural support to a body lumen and then gradually and completely degrades or is absorbed in a manner that precludes a break-up into large particles. Similarly, a biodegradable coating is needed that is not prone to flaking or breaking up into large particles. By preventing the break-up of the stent or of the stent coating into large particles that may subsequently be swept downstream, the potential for embolic complications is thereby avoided.

SUMMARY OF THE INVENTION

The present invention provides a stent or optionally, a stent coating which degrades in a very controlled and uniform manner so as to substantially preclude the possibility of sizeable particles becoming detached and possibly causing embolic problems downstream. This is achieved by employing a material in the construction of the entire stent or in the coating of the stent that erodes in a very controlled manner. Such material is selected for its strength characteristics as well as its tendency to erode from the surface inwardly rather than being subject to bulk erosion. By incorporating pharmacological agents within the material, the stent or stent coating not only eventually vanishes from within the body lumen in which it was implanted but additionally dispenses the incorporated drug in a gradual manner.

Materials that exhibit the desired surface eroding characteristics without being subject to bulk erosion include polymers wherein the degradation rate of the matrix is faster than the rate of water penetration into the interior of the polymeric mass. Such polymers are hydrophobic but have water-labile linkages interconnecting the monomers. The hydrophobic property precludes water from penetrating into the interior of the polymer while water labile linkages nonetheless subject the surface to gradual erosion. As a result, the stent gradually degrades from the surface inwardly, substantially without the risk of large particles becoming dislodged.

While hydrophobic polymers with water-labile linkages are known, their limited strength and processing capabilities have restricted their usage to passive devices that neither perform a structural function nor are subject to stress or distortion. Drugs infused throughout such material implanted in the body in the form of a tablet or other shape are gradually released as the polymer degrades. As such, these surface degrading polymers have functioned as an effective drug delivery vehicle. The use of such polymers in stent applications has however been precluded as they are unable to support a lumen wall or remain attached to a stent as it undergoes deformation during its expansion.

The materials employed in either wholly forming a stent or in coating a stent in accordance with the present invention include hydrophobic polymers having water-liable linkages connecting the monomers that are fortified with the incorporation of ester or imide bonds. Examples of such polymers include polyanhydrides and polyorthoesters. Additionally, by employing such polymers in stent applications, a single device can be called upon to provide the necessary support to a body lumen and simultaneously dispense a pharmacological agent in a controlled manner.

These and other features and advantages of the present invention will become apparent from the following detailed description of a preferred embodiments which illustrate by way of example the principles of the invention.

DETAILED DESCRIPTION OF THE PREFERRED EMBODIMENTS

The stent of the present invention is employed to support or otherwise treat a targeted site within the vasculature. Such stent is introduced into the vasculature, advanced therethrough to the deployment site and expanded using conventional techniques and delivery systems. Once in position and subject to the continuous flow of blood therethrough, it gradually degrades, substantially without the risk inherent in previously known biodegradable stents or stents with biodegradable coatings of breaking up into or releasing sizeable particles that may be swept downstream and cause emboli.

The material employed in the manufacture of the stent of the present invention is a polymer that is simultaneously hydrophobic and has water-labile linkages interconnecting its monomers that are further fortified by ester or imide bonds. The hydrophobic nature of the polymer precludes the incursion of water into its interior while the water-labile bonds that are exposed on its surface nonetheless cause the polymer to degrade. Degradation thereby exclusively progresses from the material's surface inwardly to yield a much more uniform degradation rate and to preclude bulk erosion. The incorporation of the imide or ester bonds serves to impart sufficient strength to the material to enable it to provide the support that is required of a stent. Alternatively, if the material is used as stent coating, the incorporation of the imide or ester bonds impart sufficient strength to the material to prevent it from flaking off or otherwise becoming detached as the underlying stent undergoes the distortion attendant its being expanded by for example the inflation of a balloon.

Many of the stent's ultimate performance characteristics are controllable by the appropriate selection of the various dimensional parameters of the stent. Increasing the dimensions of various structural elements of the stent will generally serve to increase strength and decrease flexibility. Such effect would result from both an increase in the width or in the wall thickness of the stent's structural elements. The time period in which the stent would become totally degraded or absorbed is a function of the wall thickness of the various elements while the degradation rate is a function of the total area exposed to contact with the blood. By for example selecting a stent configuration which employs a large number of relatively narrow spine and strut elements to achieve a particular level of strength, the time in which the stent degrades when subjected to the blood flow can be substantially accelerated. Conversely, a stent configuration in which a relatively few, wide structural elements are employed causes the degradation rate to be somewhat retarded.

The stent's ultimate performance characteristics are of course also controllable by the appropriate selection of chemical variables. For example, the number of imide or ester bonds that are incorporated in the polymer material not only affects the ultimate strength and flexibility characteristics of the stent, but also has an effect on the rate at which the material degrades when subjected to blood flow. An increased bond content enhances strength, decreases flexibility and increases degradation time. The specific requirements of a particular application will ultimately determine the optimal combination of the stent configuration, wall thickness and ester or imide bond content.

Polymers that satisfy the above-described requirements include polyanhydrides and polyorthoesters. Representative examples of polyanhydride polymers suitable for use in the construction of a stent or formulation of a stent coating in accordance with the present invention include anhydride-co-imide ter polymers containing trimellitylimido-L-tyrosine, sebacic acid (SA) and 1,3 bis(carboxyphenoxy)propane. Other examples of suitable polyanhydrides include poly(fatty acid—sebacic acid) synthesized from erucic acid and sebacic anhydride p(EAD:SA) and poly(L-lactic acid-co-L-aspartic acid). Representative examples of polyorthoester polymers suitable for use in the construction of a stent or formulation of a stent coating in accordance with the present invention include poly(4-hydroxy-L-proline ester), poly(1, 10 decanediol-1, 10 decanediol dilactide) and poly(1, 2, 6 hexanetriol-trimethylorthoacetate). An ester or imide content of 20%-40% has been found to be effective to provide sufficient strength for a stent application.

The process for forming a polymer stent is well known in the art. A stent of the present invention is formed by first causing the appropriate reagents to react to form the desired polyanhydride or polyorthoester composition. During copolymer synthesis, the imide content of such composition is increased by incorporating higher imide containing monomers like trimellitylimido-L-tyrosine. Increasing imide content results in higher strength material. Flexibility of polyanhydrides like p(EAD:SA) can be increased by increasing the percentage of erucic acid dimer (EAD) during polymer synthesis. The ester content of such composition is increased by incorporating higher ester containing monomers such as L-proline ester or trimethyl orthoacetate.

Selected pharmacological agents can be added to the reagents so as to incorporate such materials throughout the polymer to thereby provide for the gradual dispensation of the drug over the service life of the stent. The blending may be accomplished either in solution or in a melt state. Drugs such as for example heparin or other proteins can readily be added to the reactants before or during the polymerization process. Alternatively, some drugs may be infused throughout the polymer after polymerization is completed. If desired, the drug may be applied to the surface of the cured polymer to cause the entire dosage to be released shortly after implantation.

The stent may be formed by any of a number of well known methods including the extrusion of the polymer into the shape of a tube. Preselected patterns of voids are then formed into the tube in order to define a plurality of spines and struts that impart a degree of flexibility and expandability to the tube.

Alternatively, the drug loaded polymer may be applied to the selected surfaces of a stent formed of, for example, stainless steel or Nitinol. In order to coat all of the surfaces of the stent, the stent is immersed in the molten polymer. Alternatively, the polymer may be extruded in the form of a tube which is then co-drawn with a tube of stainless steel or Nitinol. By co-drawning two tubes of the polymer with a metal tube, one positioned about the exterior of the metal tube and another positioned within such metal tube, a tube having multi-layered walls is formed. Subsequent perforation of the tube walls to define a preselected pattern of spines and struts imparts the desired flexibility and expandability to the tube to create a stent.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed:

1. A coated stent comprising:
   a stent body in a size suitable for implantation in a blood vessel; and
   a coating covering at least a portion of the stent body, the coating including a biodegradable terpolymer having three different types of units from three different monomers and comprising anhydride-derived and imide-derived units,
   wherein the terpolymer is bulk-erosion resistant when implanted into a lumen of a patient and subjected to blood flow.

2. The coated stent of claim 1 wherein the terpolymer comprises a polyanhydride or a polyorthoester.

3. The coated stent of claim 1 wherein the terpolymer is loaded with a pharmacological agent.

4. The coated stent of claim 3 wherein the pharmacological agent comprises heparin.

5. A coated stent comprising:
a stent body in a size suitable for use in a blood vessel; and
a coating covering at least a portion of the stent body, the coating including a biodegradable terpolymer having three different types of units from three different monomers and comprising anhydride-derived and imide-derived units in the amount of 20% to 40% of the polymer,
wherein the terpolymer is bulk-erosion resistant when implanted into a lumen of a patient and subjected to blood flow.

6. The coated stent of claim 5 wherein the polymer is hydrophobic.

7. The coated stent of claim 5 wherein the coating additionally includes a pharmacological agent.

8. The coated stent of claim 7 wherein the pharmacological agent comprises heparin.

9. The coated stent of claim 7 wherein after the stent is implanted into a lumen of a patient and the coating is subjected to blood flow, the pharmacological agent is gradually released from the coating.

10. The coated stent of claim 5 wherein the stent body comprises a metallic material.

11. A coated stent comprising:
a stent body; and
a coating covering at least a portion of the stent body, the coating including a biodegradable terpolymer having three different types of units from three different monomers and comprising anhydride-derived and imide-derived units in the amount of 20% to 40% of the polymer,
wherein the terpolymer is bulk-erosion resistant when implanted into a lumen of a patient and subjected to blood flow, and
wherein the terpolymer has a degradation rate that is faster than the rate of water penetration into the interior of the polymer after the stent is implanted into the lumen of the patient.

12. A coated stent comprising:
a stent body; and
a coating covering at least a portion of the stent body, the coating including a biodegradable terpolymer having three different types of units from three different monomers and comprising anhydride-derived and imide-derived units in the amount of 20% to 40% of the polymer,
wherein the terpolymer is bulk-erosion resistant when implanted into a lumen of a patient and subjected to blood flow, and
wherein the terpolymer further comprises a biodegradable polymer comprising fragments having water-labile ester or imide bonds.

* * * * *